US006656512B1

(12) United States Patent
Fone et al.

(10) Patent No.: US 6,656,512 B1
(45) Date of Patent: Dec. 2, 2003

(54) PET FOOD PRODUCT WITH COCONUT ENDOSPERM FIBER

(75) Inventors: Janel Fone, Melton Mowbray (GB); Catriona J. Giffard, Leicestershire (GB); Marie-Louise Baillon, Leicestershire (GB)

(73) Assignee: Mars UK Limited (GB)

( * ) Notice: Subject to any disclaimer, the term of this patent is extended or adjusted under 35 U.S.C. 154(b) by 0 days.

(21) Appl. No.: 09/936,036

(22) PCT Filed: Mar. 10, 2000

(86) PCT No.: PCT/GB00/00890

§ 371 (c)(1),
(2), (4) Date: Dec. 27, 2001

(87) PCT Pub. No.: WO00/53030

PCT Pub. Date: Sep. 14, 2000

(30) Foreign Application Priority Data

Mar. 10, 1999 (GB) .............................................. 9905542

(51) Int. Cl.⁷ .................................................. A23K 1/14
(52) U.S. Cl. ............................. 426/2; 426/661; 426/805
(58) Field of Search ............................. 426/2, 661, 805

(56) References Cited

FOREIGN PATENT DOCUMENTS

| AU | 9352616 | * | 7/1994 |
| JP | 6-340863 |  | 7/1996 |
| JP | 08173055 | * | 7/1996 |
| WO | WO91/03754 |  | 12/1991 |
| WO | WO96/39046 |  | 12/1996 |

OTHER PUBLICATIONS

Etude des fibres alimentaires chez le chien: presentation des resultats de 7 essais experimentaux; Ann. Med. Vet., 1998, 142, 185–201.

* cited by examiner

Primary Examiner—Chhaya Sayala
(74) Attorney, Agent, or Firm—Fulbright & Jaworski, LLP.

(57) ABSTRACT

The present invention relates to the use of coconut endosperm fiber as a dietary fiber component in a pet food product, to the use of coconut endosperm fiber in the manufacture of a pet food product, to a pet food product which comprises coconut endosperm fiber, to a process for making such a pet food product and to a method comprising feeding such a pet food product to a pet animal. The present invention also relates to the use of coconut endosperm fiber in reducing and preventing intestinal inflammation and in reducing and preventing pathogenic bacterial infection in the large intestine of a pet animal.

30 Claims, 2 Drawing Sheets

COMPARISON OF TWO PRODUCTS CONTAINING
COPRA PRESSCAKE

COMPARISON OF MEAN FAECES SCORES FOR EACH DIET
SAME LETTER MEANS NOT SIGNIFICANTLY DIFFERENT
(ANOVA, $p > 0.05$)

|  | DIET 1 | DIET 2 |
|---|---|---|
| MEAN SCORE: | 2.3 | 2.3 |
| No. DEFAECATIONS: | 200 | 207 |

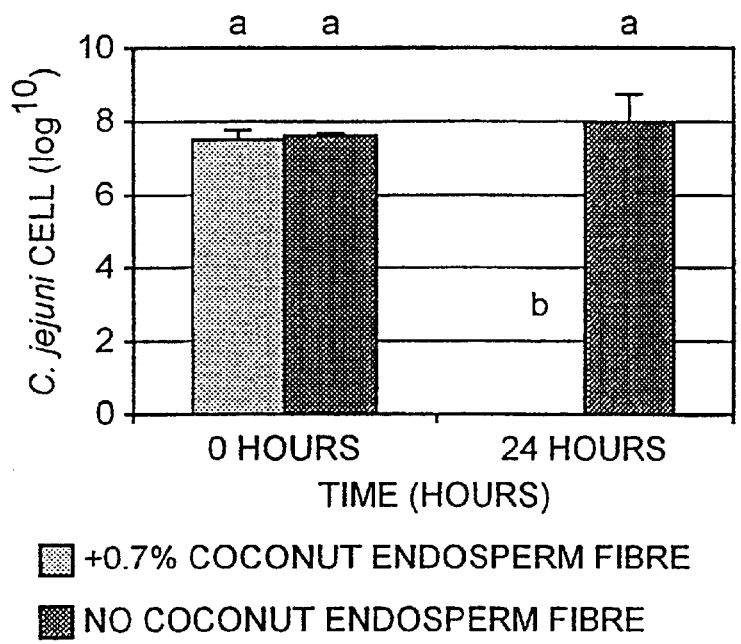
FIG. 2
FIG. 3
MEAN $PGE_2$ PRODUCTION BY COLONIC BIOPSY SAMPLES
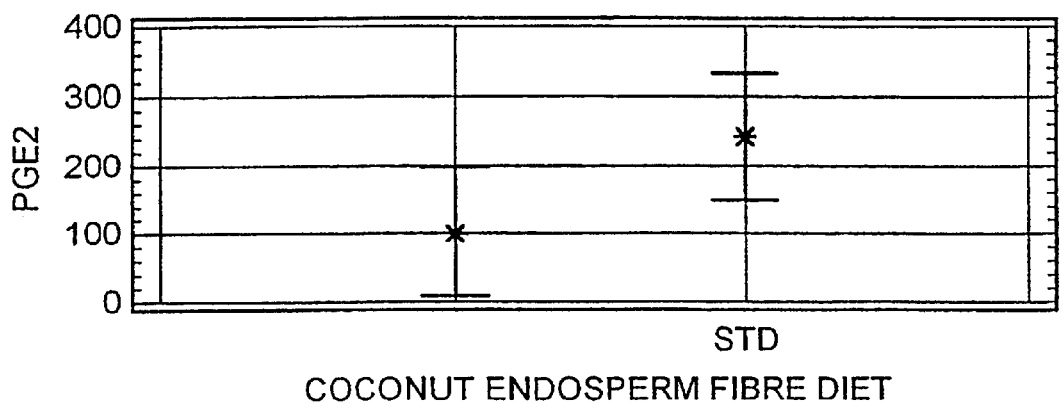

PET FOOD PRODUCT WITH COCONUT ENDOSPERM FIBER

The present invention relates to the use of coconut endosperm fibre as a dietary fibre component in a pet food product, to the use of coconut endosperm fibre in the manufacture of a pet food product, to a pet food product which comprises coconut endosperm fibre, to a process for making such a pet food product and to a method comprising feeding such a pet food product to a pet animal. The present invention also relates to the use of coconut endosperm fibre in reducing and preventing intestinal inflammation and in reducing and preventing pathogenic bacterial infection in the large intestine of a pet animal.

The maintenance and improvement of pet health is a constantly ongoing aim in the art. Pet health can be monitored in a number of ways. Two of these are faeces quality and gastrointestinal (GI) tract health. Good quality faeces in pet animals is of two-fold importance. Firstly, it is a good indicator of a healthy pet. It is known that good faeces quality usually reflects healthy colonic structure and function. Secondly, it is a much favoured practicality for pet-owners. Accordingly, the maintenance of good quality pet faeces and the ability to improve the quality of pet faeces is a constantly ongoing aim in the art. It is also an ongoing aim in the art to improve the GI tract health of pet animals. The ability to maintain and improve GI tract health can be beneficial to pet owners because it has an impact on their pet's overall health.

One method for maintaining normal gastrointestinal function and ameliorating chronic diarrhoea in animals has included the addition, in pet food products, of a fibre source.

Fibre has wide ranging effects on bowel habit, increasing faecal output, reducing transit times and altering colonic metabolism. Many of the beneficial effects of fibre relate to its extensive breakdown in the large intestine. This anaerobic process, termed fermentation, is the principle metabolic event occurring in the colon. Fermentation is a digestive function of the complex assemblage of microorganisms that inhabit the large intestine, which break-down complex carbohydrates and other substrates that have not been hydrolysed and absorbed in the upper intestine. Both the microbiotia and the host benefit from this association.

Many hundreds of bacterial types, varying widely in physiology and biochemistry, reside within the colon. Characterising the individual activities of this multipotent microflora is an immensely complex undertaking and is unclear even in the human field. However, some understanding of the role of the microflora in the colon can be gained by quantifying the fermentation activity of the bacterial population as a whole.

The major complex carbohydrate fermentation products are short chain fatty acids (SCFAs), gases and energy. The energy generated is used for microbial cell growth which routes much of the colonic nitrogen into bacterial protein and increased microbial mass. SCFAs are rapidly absorbed and can influence gastrointestinal function by providing energy substrates to the colonic mucosa and by promoting water and electrolyte adsorption from the colonic lumen. Gas produced during fermentation is eliminated both through the lungs and as flatus. In a carbohydrate-limited environment, bacteria will resort to the breakdown of protein which provides much less energy in the form of branched chain fatty acids and also metabolites that are potentially toxic to the host (ammonia, amines, phenols etc.). It is one object of the present invention to incorporate, into pet food products, a useful dietary fibre.

In the production (or manufacture) of commercial pet food products, a small number of different technologies are used. In all cases, product components are mixed together (often, but not necessarily with cooking/heating) with optional other components added later on, and then transported to the various containers to be filled. The process may include extrusion cooking, for example in the production of a dry product. Alternatively, the process may include emulsion milling in the production of "chunks". A variety of processes will include the pumping of the product from one part of the processing apparatus to another and optionally further into cans. It is always desirable to obtain a combination of ingredients which maximise the processing of the ingredients through to the final product. It is a further object of the present invention to provide a dietary fibre which is particularly suitable in the manufacturing process.

The present invention relates to providing, in a pet food product, a useful fibre source. The fibre source is particularly easy to use in the manufacture of a pet food product.

Accordingly, a first aspect of the invention provides the use of coconut endosperm fibre as a dietary fibre component in a pet food product. The first aspect of the invention includes the use of coconut endosperm fibre as a dietary fibre component in the manufacture of a pet food product.

The coconut endosperm fibre may be used as the single dietary fibre component or in combination with one or more other dietary fibre components, such as beet pulp, chicory, citrus pulp, rice bran, carob bean or gum talha.

Fresh coconut endosperm has a typical nutrient distribution of water (35%), oil (44%), protein (6%), sugars (7%), fibre (3%) and ash (1%). However, the form of the coconut endosperm fibre for use according to all aspects of the present invention is not limiting. The coconut endosperm fibre may be fresh or in any other form such as copra defatted copra (also referred to, amongst others, as copra cake, copra presscake or copra meal) coconut flour, defatted coconut flour, full or defatted desiccated coconut, copra, or degraded coconut endosperm which has been heated or enzymatically treated.

Copra is a particularly suitable source of coconut endosperm fibre for use according to the present invention. Copra is dried coconut endosperm (usually sundried). Defatted copra is also particularly suitable. Defatted copra is the typical result of coconut endosperm which has been dried and had the coconut oil mechanically removed. Defatted copra cake is obtained by first obtaining copra, then crushing the copra through a press or expeller to remove most of the oil. The residue remaining is termed copra cake, copra presscake, or copra meal.

Without limiting the present invention, the addition of coconut endosperm fibre into a pet food product is believed to i) maintain good faeces quality or improve the faeces quality of a pet and/or ii) maintain good GI tract health or improve it, either achieved by one or more of the following: the improvement of faeces water binding, the reduction of faecal pH, the increased production of beneficial end products and decreased production of detrimental end products of microbial fermention, the enhancement of populations of beneficial bacteria, the enhancement of water/electrolyte uptake in the gastrointestinal tract, the improvement of colonic structure/health and the provision of good water binding features to equalise faecal texture. The present invention is useful for healthy animals, including sensitive animals as well as animals that suffer from poor faeces quality or poor GI tract health. Accordingly, the first aspect of the invention also relates to the use of coconut endosperm fibre in the manufacture of a pet food product for use in maintaining or improving the faeces quality of a pet animal, or for use in maintaining or improving GI tract health. Poor faeces quality is described in Appendix 1

Evaluation of faeces quality and the identification of maintenance or improvement of faeces quality are techniques well known and used in the art. More than one method can be used (alone or in combination). Methods commonly use a panel of trained observers (may be trained members of the public or professionals). Faecal samples from a pet are collected and may be scored according to a rating system outlined in Appendix 1. The evaluation of good faecal quality is determined according to faecal quality which often reflects a normal gastrointestinal function. This is usually the formation of a stool which is firm and retains its shape. Stools which are hard, pellet-like and dry (and may be produced with straining), or which are produced with a moisture content such that shape is not retained (including diarrhoea), do not represent normal gastrointestinal function. The precise optimum stool consistency may vary somewhat between different types of pet animals and between species of an animal, but can be easily determined on review by a person skilled in the art.

Evaluation of good GI tract health and the identification of improvement of GI tract health are also techniques well known and used in the art. The evaluation of maintained or improved GI health can be determined by comparison of a pet animal fed on the same diet but without the coconut endosperm fibre. Colonic (or intestinal or digestive) health can be defined in terms of stool quality and pH, the presence and numbers of beneficial and potentially harmful bacteria in the lumen of the GI tract and/or faeces and total and specific short chain fatty acids. The study of such features in vivo is difficult, not only due to the inaccessability of the large intestine and the difficulty in collecting its contents, but the additional complication that SCFAs produced in the colon are metabolised at a number of sites in the body from which there is no prospect of obtaining samples without adopting invasive technologies. In vitro fermentation systems that use faeces as an inoculum can be used as simple, rapid (although specifically indefinable) methods which can be used to predict some of the physiological effects of fibre in vivo. In this respect, an understanding of the beneficial role of the microflora in the colon can be gained by quantifying the fermentation activity of the beneficial population as a whole. SCFA production, as measured in an in vitro fermentation system, provides an indicator of bacterial activity (see Example 3).

The present invention has been shown to be particularly useful in the ability to increase the production of butyrate from the fermentation of coconut endosperm fibre and thus increase the availability of butyrate in the gut. Butyrate is one SCFA of particular interest due to the trophic effects it can exert on colonocytes, as well as its beneficial metabolic role. Using the coconut endosperm fibre of the present invention, increased levels of butyrate production (in vitro tests) were observed alongside increased values seen with substrates known to produce high levels of butyrate, such as inulin, in the same test system.

Coconut endosperm fibre is also a useful component of the invention due to its role in preventing or treating pathogenic bacterial infection in an animal's large intestine. Pathogenic infection in the large intestine may be clinical or sub-clinical. Both types of infection are deleterious to the health of the animal and to the animal's faeces quality. More details on the role of coconut endosperm fibre are described below in relation to the sixth and seventh aspects of the invention. The details as given for the sixth and seventh aspects of the invention also apply to the first to fifth aspects of the invention.

Furthermore, and in addition to the above described beneficial effects of coconut endosperm fibre, it has also now been shown that coconut endosperm fibre in a pet food product reduces the inflammatory status of an animal's colon or maintains a low inflammatory status of an animal's colon. More details on the role of coconut endosperm fibre in reducing the inflammatory status of an animal's colon are described below in relation to the eighth and ninth aspects of the invention.

In combination with the coconut endosperm fibre source, the remaining components of the pet food product are not essential to the invention and typical standard products can be combined with the required coconut endosperm fibre content. Most preferably, the combined ingredients of the pet food product according to the invention provide all of the recommended vitamins and minerals for the particular pet in question, (a complete and balanced food), for example, as described in National Research Council, 1985, Nutritional Requirements for Dogs, National Academy Press, Washington D.C. (ISBN: 0-309-03496-5); National Research Council, 1986, Nutritional Requirements of Cats, National Academy Press, Washington D.C. (ISBN: 0-309-03682-8) or Association of American Feed Control Officials, Official Publication 1996.

The coconut endosperm fibre sources of the present invention are, for a further reason, also particularly useful and effective as a component of a pet food product. This is because the fibre source, in most cases, will contain useful levels of other nutritional factors, such as fat and protein. The presence of such other nutritional factors is due to their presence (and the proportions of their presence) in the originating source of the fibres (the coconut endosperm). It is known that coconut oil is high in medium chain fatty acids (MCFAs) and that such MCFAs are more readily absorbed in the gut of animals. Accordingly, the coconut oil present in the source of the coconut endosperm fibres (even in defatted copra cake, which contains in the region of 5–10% fat on a dry matter basis) provides a key nutritional factor for the animal. Since such oil is a particularly good source of readily absorbed fatty acids, the presence of the oil in the fibre source is especially useful in certain groups of compromised pet animals.

The level of coconut endosperm fibre incorporated into a pet food product as a dietary fibre component is not limiting. Preferably, the fibre component of coconut endosperm is present in the pet food product at a level of from approximately 0.15 to 8% on a dry matter basis, preferably 0.15 to 5% on a dry matter basis as measured by the Englyst method (as defined in Englyst H. N., and Cumming J. H. (1984), Simplified method for the measurement of total non-starch polysaccharides by gas-liquid chromatography of constituent sugars as alditol acetates. Analyst. 109, 937–942, and incorporated herein by reference). The levels, as calculated by this method, may go from. 0.15% up to 5%, 6%, 7% or 8%. The lower limit may be from 1.5%, 2% or 3%. A description of the Englyst method is described in Appendix 2. In principle, starch is removed enzymatically after solubilisation and NSP is measured as the sum of the constituent sugars released by acid hydrolysis. The starch component of the fibre source is gelatinised by boiling in hot water and is then removed with alpha-amylase and pullulanase. Starch and modified, or resistant starch are dispersed in DMSO. Three samples are then subjected to complementary procedures measuring (i) total NSP (ii) water-soluble NSP and (iii) cellulose. Components are hydrolysed in each case with sulphuric acid. The constituent sugars are converted to alditols and are measured as their alditol acetates using gas-liquid chromatography (GLC). Values for total dietary fibre as well as insoluble and soluble fractions can be obtained. Cellulose can be measured separately and the non-cellulosic polysaccharides are characterised by measurement of the individual monosaccharides.

The incorporation of the level of coconut endosperm fibre, (which may differ according to the form of the coconut endosperm, for example copra or desiccated coconut) can easily be determined by identifying the amount of dietary fibre in the particular form of the coconut endosperm fibre. For example, according to the Englyst method (Supra) defatted copra contains approximately 33.5% total dietary fibre. Accordingly, the preferred amount of defatted copra in a pet food product in order to provide a preferred fibre level of from approximately 0.15 to 5% on a dry matter basis according to the first aspect of the invention is at a level from approximately 0.5 to 15% on a dry matter basis of the pet food product.

These ranges apply to the first aspect of the invention for a variety of pet animals. The invention is particularly applicable to mammalian pet animals, especially dogs, cats and horses.

The pet food product according to the present invention is preferably a commercial pet food product. Such a product is preferably sold as a product for feeding to a pet animal, in particular a pet cat or a pet dog.

The pet food product is preferably packaged. In this way, the consumer is able to identify, from the packaging, the ingredients in the food product and confirm that it is suitable for the particular pet in question. The packaging may be metal (usually in the form of a tin or flexifoil), plastic, paper or card. The pet food may be a dry, semi-moist or a moist product. Wet food includes food which is sold in tins and has a moisture content of 70 to 90%. Dry food includes food having a similar composition, but with 5 to 15% moisture and presented as small biscuit-like kibbles. The amount of moisture in any product may influence the type of packaging which can be used or is required.

The pet food product according to the present invention encompasses any product which a pet consumes in its diet. Thus, the invention covers standard food products as well as pet food snacks (for example, snack bars, cereal bars, snacks, biscuits and sweet products). The food product is preferably a cooked product. It may be in the form of a gelatinized starch matrix. It may be in the form of chunks in gravy, jelly, loaf or water. It may incorporate meat or animal derived material (such as beef, chicken, turkey, lamb, pork, fish, blood plasma, marrow bone etc or one or more thereof). The product alternatively may be meat free (preferably including a meat substitute such as soya, maize gluten or a soya product) in order to provide a protein source. The product may contain additional protein sources such as soya protein concentrate, milk proteins, gluten etc. The product may also contain a starch source such as one or more grains (e.g. wheat, corn, rice, oats, barley etc), or may be starch free. A typical dry dog or cat food contains about 20–30% crude protein, about 10–20% fat, the remainder being carbohydrate, including dietary fibre and ash. A typical wet or moist product contains (on a dry matter basis) about 40% fat, 50% protein and the remainder being fibre and ash. The present invention is particularly relevant for a pet food product as herein described which is sold as a pet food, in particular, a pet food for a dog or a cat. Cats and dogs according to the present invention are preferably *Felis domesticus* or *Canis domesticus*.

A second aspect of the invention provides the use of coconut endosperm fibre in the manufacture of a pet food product. The second aspect of the present invention does not include such a use to manufacture a pet food product which includes a gel comprising coconut endosperm and carrageenan. Such a pet food product, which includes a gel comprising coconut endosperm and carrageenan has previously been described in WO96/39046. The disclosure in WO96/39046 is limited to a gelling system comprising carrageenan and coconut endosperm. The use of the endosperm in WO96/39046 is only as a component of a gelling system.

The use of coconut endosperm fibre in the manufacture of a pet food product (in accordance with the second aspect of the invention) has the advantages described above according to the first aspect of the invention. In addition, it has been determined, by the present inventors, that coconut endosperm fibre sources are particularly suitable dietary fibres for a pet food manufacturing process. The use of coconut endosperm as a dietary fibre is extremely satisfactory. The coconut endosperm fibre advantageously and surprisingly generates less emulsion viscosity when added to the remainder of the product ingredients compared to the use of other fibre sources. The advantages of such a fibre are especially noted in the process of pumping and forming the product. It is particularly useful in the process of "emulsion milling" in the production of "chunks". Further the use of a coconut endosperm fibre source does not lead to a grey colour, following processing, often associated with some other fibre sources. Instead, an aesthetically acceptable colour is obtained.

Preferred features of the first aspect of the invention, also apply to the second.

A third aspect of the invention provides a pet food product which comprises coconut endosperm fibre. The third aspect of the present invention does not include a pet food product which includes a gel comprising coconut endosperm and carrageenan as in WO96/39046. The pet food product according to the third aspect of the invention has the advantages as described above for the first and second aspects of the invention. These include; the promotion of good faeces quality and GI health, in particular the levels of the SCFA butyrate following fermentation, and surprisingly good processing qualities. The pet food product is particularly suitable for feeding to a pet animal.

All preferred features of the first and second aspect also apply to the third. These include levels and sources of coconut endosperm fibre, types of food products, manufacturing and other components of the food product.

A fourth aspect of the present invention provides a process for preparing a pet food according to the third aspect of the invention comprising mixing the ingredients with optional heating/cooking. The pet food product may be formed before or after the mixing and/or the heating/cooking.

As described above, the incorporation of coconut endosperm fibres provides a number of advantages over the incorporation of other fibres in the process for preparing a pet food product and in the resulting pet food product.

The process comprises mixing a source of coconut endosperm fibre with one or more ingredients of a pet food product. The product can in all other ways be produced by processes known in the art. The coconut endosperm fibre may be added prior to or following heating or cooking of one or more of the other ingredients. The process may also include the step of extracting the coconut endosperm fibre from coconut material.

The food product can be made according to any method known in the art, such as in Waltham Book of Dog and Cat Nutrition, Ed. ATB Edney, Chapter by A. Rainbird, entitled "A Balanced Diet" in pages 57 to 74 Pergamon Press Oxford.

All preferred features of aspects one to three, also apply to the fourth. These include levels and sources of coconut endosperm fibre, types of food products, manufacturing and other components of the food product.

A fifth aspect of the invention provides a method comprising feeding a pet animal a pet food product according to the third aspect of the invention. The fifth aspect of the invention includes a method for maintaining or improving gastrointestinal tract health in a pet animal, the method comprising feeding the animal a pet food product according to the third aspect of the invention. Feeding the pet animal with the pet food product according to the third aspect of the invention maintains or improves the GI health of the animal by the presence of the coconut endosperm fibre. The animal is fed the pet food product in a sufficient quantity and for a sufficient time period in order to maintain or improve the GI health. A particular GI health improvement is due to the SCFA production, in particular butyrate production.

The fifth aspect of the invention includes a method for maintaining or improving faeces quality in a pet animal, the method comprising feeding the animal a pet food product according to the third aspect of the invention.

Feeding the pet animal with the pet food product according to the third aspect of the invention maintains or improves faeces quality by the presence of the coconut endosperm fibres. The animal is fed the pet food product in a sufficient quantity and for a sufficient time period in order to maintain or improve faeces quality.

The quantity and time period for feeding according to the fifth aspect of the invention will depend on a number of factors including type of animal, breed, age and general state of health, which the pet feeder can easily use to determine quantity of food and time period for feeding.

The method of the fifth aspect may be, but is not restricted to, veterinarian treatment. The feeding may be non-therapeutic. The term "feeding" also including the meaning of "administration" to an animal. The methods may be prophylactic or therapeutic. The preferred features of the first to fourth aspects of the invention also apply to the fifth aspect. These include levels and sources of coconut endosperm fibre, types of food products, manufacturing and other components of the food product.

A sixth aspect of the invention provides for the use of coconut endosperm fibre in the manufacture of a pet food product for the prevention or treatment of pathogenic bacterial infection in the large intestine of a pet animal.

Infection of the large intestine, in a pet animal, by pathogenic bacteria is concerning. Particular pathogenic bacteria include Campylobacter (especially *Campylobacter jejuni*), Salmonella and *Escherichia coli*. *Campylobacter jejuni*, the species responsible for the majority of human infections, is also the main species of concern for cats and dogs. The species can act as a pathogen in young dogs and cats and is likely to be opportunistic in older animals. Clinical illness in dogs manifests itself as diarrhoea, ranging from mild to mucus laden bloody diarrhoea, tenesmus, vomiting, anorexia and depression. A major concern regarding Campylobacter infection in companion animals is the zoonotic risk that carriage and excretion of the organism represents. It has been estimated that 5% of all human *C. jejuni* induced diarrhoea results from exposure to infected dogs or cats. A number of more recent studies quote dog ownership as a significant risk factor for becoming ill with Campylobacter. A study conducted in Christchurch, New Zealand found that household contact with dogs carried a risk of 1.25 to 2 times for contracting Campylobacter. In addition, there are concerns that attempts to reduce and eliminate Campylobacter infection by continued use of antibiotic strains may lead to the emergence of antibiotic resistant strains of this organism.

The present invention of a pet food product comprising coconut endosperm fibre has been shown to be effective in preventing and treating pathogenic bacterial infection in the large intestine of a pet animal. The animal is, in particular, a cat or a dog (in both cases, preferably *Felis domesticus* or *Canis domesticus*). Pathogenic bacteria include, amongst others, Campylobacter, Salmonella, pathogenic Clostridium and *E. coli*, such as enteropathogenic *E. coli* and verotoxigenic *E. coli*.

A seventh aspect of the invention provides a method for preventing or treating pathogenic bacterial infection in the large intestine of a pet animal, the method comprising feeding said pet animal a pet food product comprising coconut endosperm fibre.

An eighth aspect of the invention provides for the use of coconut endosperm fibre in the manufacture of a pet food product for the prevention or treatment of intestinal inflammation in a pet animal.

In dogs, an inflammatory response in the colon is associated with the production of various mediators, including the eicosanoid prostaglandin E2 ($PGE_2$).

The present invention shows that pet animals which are fed a pet food product comprising coconut endosperm fibre produce significantly less $PGE_2$ than the same diet without a fibre source.

A ninth aspect of the invention provides a method for preventing or reducing intestinal inflammation in a pet animal, the method comprising feeding said pet animal a pet food product containing coconut endosperm fibre.

In accordance with the sixth, seventh, eighth and ninth aspects of the invention, the animal is a canine animal. The coconut endosperm fibre may be in any form and preferably as described for the first to fifth aspects of the invention. The coconut endosperm fibre is preferably present at a level of from 0.15 to 5%, on a dry matter basis, in the pet food product, as measured by the Englyst method. All other preferred features are as for the first to fifth aspects of the invention.

The invention is described with reference to the figures, in which

FIG. 2 shows a graph of the effect of the inclusion of coconut endosperm fibre in the canine large intestine model on the survival of *Campylobacter jejuni*; and FIG. 3 shows mean eicosanoid prostaglandin $E_2$ production by colonic biopsy samples.

Figure 1:
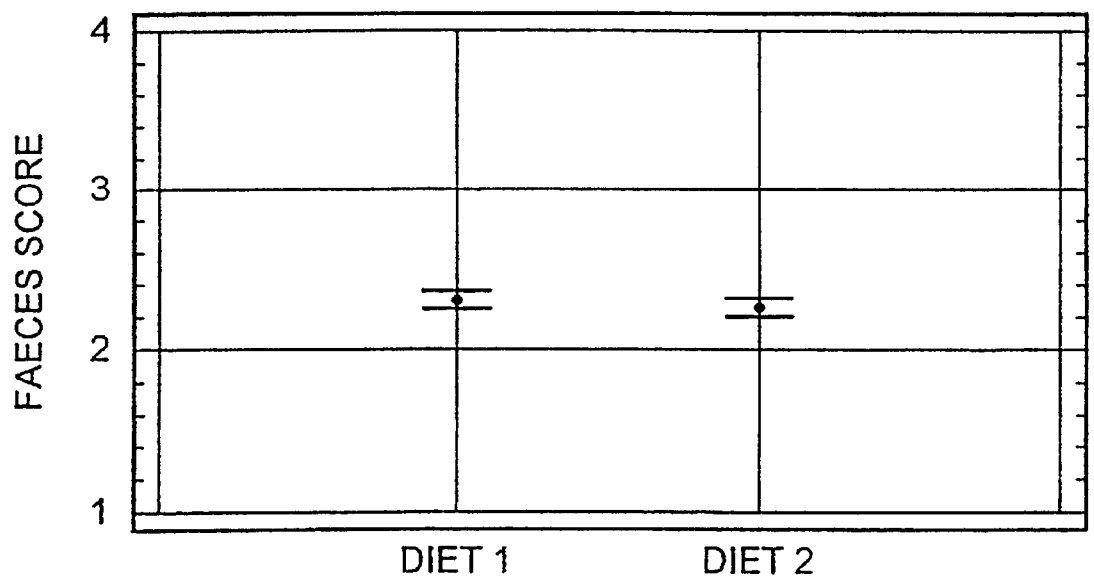
FIG. 1 shows a comparison of faeces scores between two diets containing copra presscake.

The invention will now be described with reference to the following, non-limiting examples:

EXAMPLE 1

This example describes the preparation and use of defatted dried coconut flour.

Coconuts were obtained from the local market and the white flesh or endosperm recovered. The endosperm was finely ground and repeatedly extracted with acetone to remove the fat and water. A dried defatted coconut powder was obtained.

EXAMPLE 2

This example describes the preparation of mechanically defatted copra cake.

Coconut endosperm, stripped from a coconut was crushed. The crushed material was heated to a maximum 120° C. using techniques widely known in the art of oilseed processing, and passed through a hydraulic press or expeller to remove most of the oil. The extract obtained by this process was dried, if necessary to obtain a product with a moisture content of approximately 15%.

EXAMPLE 3

Evaluation of coconut endosperm fibre as a dietary fibre.

Raw Materials

The raw material evaluated in this in vitro fermentation system is particularly suitable for addition to dry and canned dog and cat products

TABLE 1

| Fibre Sources | |
|---|---|
| Raw Material | Physical Appearance |
| Defatted Copra Presscake | Coarse grained orange/brown particles |

The raw material was analysed for total dietary fibre using Englyst and AOAC methodologies (Table 2.) The AOAC methodology can be found in AOAC International 1995, Total, Soluble and Insoluble Dietary Fibre in Foods. AOAC Official method 991 43, Official Methods of Analysis, $16^{th}$ Ed. The Englyst methodology is referred to previously in this text and in Appendix 2. Dietary fibre analysis revealed significant differences in total dietary fibre levels between the raw materials. Analysis by AOAC generally produced a higher percentage of total dietary fibre compared with analysis by Englyst. The Englyst technique uses enzymic-chemical methods to measure non-starch polysaccharides (NSP), the major structural components of plant cell walls, which encapsulates the more traditional definition of dietary fibre. The AOAC technique measures fibre using a combination of enzymatic and gravimetric methods that incorporate lignin and some resistant starch leading to the higher total dietary fibre levels.

TABLE 2

Raw Material Analysis for Total Dietary Fibre (TDF) by AOAC and Englyst Methodologies

| | AOAC | | | Englyst | | |
|---|---|---|---|---|---|---|
| FIBRES | % TDF | SOLUBLE | INSOL-UBLE | % TDF | SOLUBLE | INSOL-UBLE |
| Deffated Copra Presscake | 42.5 | 2.4 | 40.1 | 33.5 | 3.4 | 30.4 |

As the dietary fibre content (Englyst) of copra cake was below 40%, further analysis was carried out to determine the remaining proximal constituents of this fibre source (Table 3). The contents of non-fibre constituents were mainly protein (20.8%). The protein and free sugar constituents of copra cake could contribute artificially to the end-products of the fermentation process as they might not reach the large intestine in vivo. However, the digestibility of these fibre source macronutrients is dependent on their accessibility to the host's intestinal amylases and proteases in the small intestine. The proximal nutrients of copra cake are present at relatively small amounts therefore fibre sources have been considered on an "as is" basis.

TABLE 3

Proximate, free sugar and starch analysis of raw materials

| FIBRES | Free Sugars | Starch | Gelatinised Starch | Protein | Fat | Moisture | Ash |
|---|---|---|---|---|---|---|---|
| Defatted Copra Presscake | 7.7 | 0 | 0 | 20.8 | 8.2 | 10.8 | 5.7 |

Methodoloy

A simple approach was adopted to characterise fermentation of fibre in vitro. Similar techniques have been reported by Brøbech Mortensen P., Hove, H., Rye Clausen, M. and Holtug, K. (1991) Fermentation to short-chain fatty acids and lactate in human faecal batch cultures. *Scand. J. Gastroenterol.* 26, 1285–1294, Tigemeyer, E. C., Bourquin, L. D., Fahey, G. C. and Garleb, K. A. (1991) Fermentability of various fibre sources by human faecal bacteria in vitro. *Am. J. Clin. Nutri.* 53, 1418–1428, Sunvold, G. D., Fahey, G. C., Merchen, N. R. and Reinhart, G. A. (1995) In vitro fermentation of selected fibrous substrates by dog and cat faecal inoculum: Influence of diet composition on substrate organic matter disappearance and short-chain fatty acid production. *J. Anim. Sci.* 73, 1110–1122 and Edwards, C. A., Gibson, G., Champ, M., Jensen, B—B., Mathers, J. C., Nagengast, F., Runney, C. and Quehl, A. (1996) In vitro method for quantification of the fermentation of starch by humam faecal bacteria. *J. Sci. Food Agric.* 71, 209–217. Such systems, including the one used herein, are useful as an in vitro test to look at the results of faecal fermentation. However, such tests are not specific and cannot be defined absolutely due to inherent variation in any one animal's faecal microflora, amongst other reasons.

Fibre Sample Preparation (Day 1)

Fibre substrates were provided as copra cake at a concentration of 0.7% (w/v). 0.231 g (±0.05 g) of copra cake was weighed into triplicate 60 ml glass serum bottles (Jencons) and the exact weight recorded. 30 mls of fermentation media (Table 4) was added and bottles were capped with a cotton wool bung and were covered with metal foil.

Six bottles were prepared with no fibre source to act as controls.

200 mls of 10 mM sodium phosphate buffer, pH 7.4 and 200 mls of fastidious anaerobe broth (FAB) were prepared in conical flasks, containing a flea, for faecal resuspension. Bottles were sterilised by autoclaving (15 min, 121° C.). Bottles were placed into the anaerobic cabinet (Don Whitley) to pre-reduce immediately post autoclaving.

TABLE 4

Fermentation media composition

| Fermentation Media | 1 litre |
|---|---|
| Yeast extract | 2 g |
| Peptone water | 2 g |
| Cysteine HCl | 0.5 g |
| Vitamin K (d = 0.967 g/ml) | 5 μl |
| Tween 80 | 2 ml |
| Salt solution | 40 ml |
| Hemin solution | 5 ml |
| Indicator solution | 5 ml |

Salt solution

| $CaCl_2.6H_2O$ | 0.2 g | Into 300 mls $H_2O$ |
| $MgSO_4.7H_2O$ | 0.2 g | |
| NaCl | 2 g | into 500 mls $H_2O$ |
| $K_2HPO_4$ | 1 g | |
| $KH_2PO_4$ | 1 g | |
| $NaHCO_3$ | 10 g | | make up to 1 litre with $H_2O$

Hemin solution

| KOH | 0.28 g |
| EtOH 95% | 25 ml |
| Hemin | 0.1 g | make up to 100 ml with $H_2O$

Indicator solution

| Rezasurin | 0.02 g | make up to 100 ml with $H_2O$

Cats and Dogs

Cat or dog faeces were used as a source of bacterial inoculum for the in vitro fermentation system. Cats were fed the following dry complete diet for at least 3 months prior to the start of the study. Dogs were fed the following dry diet formulated for adult maintenance for at least 2 months prior to the start of the study.

Recipes for dry products:

| | Cat | Dog |
|---|---|---|
| Poultry | 35 | 30 |
| Cereals (rice & maize) | 55 | 60 |
| Minerals | 5 | 5 |
| Fat | 5 | 5 |
| Total | 100 | 100 |

Cats were housed in lodges to enable collection of fresh faeces for a 3 week period with a subsequent one week break. Cats were fed diets solus in amounts required to maintain body weight and had access to fresh water at all times.

Dogs were fed diets solus in amounts required to maintain body weight and had access to fresh water at all times.

Faecal Inoculation (Day 2)

A fresh faecal sample was collected. 20 g of wet faeces were added to the pre-reduced phosphate buffer within 60 min of defecation. The flask was placed on a magnetic stirrer in the anaerobic cabinet to generate a faecal resuspension slurry (approx. 10 min on stirrer). Cotton wool bungs were removed and 3 mls of this 10% (w/v) faecal slurry were aliquoted into each serum bottle that contained a fibre source and three of the control bottles with no fibre added within the anaerobic cabinet. This provided an approximately 1% faecal inoculum level within each bottle. Triplicate bottles were inoculated to cover three time point measurements. Butyl rubber caps replaced the cotton wool bungs and a metal cap was used to seal each bottle.

Three control bottles with no fibre were not inoculated and acted as media controls. Three bottles with no fibre were inoculated and were used as media and faeces controls. Bottles were incubated at 37° C. in the anaerobic cabinet. Time point measurements were taken at 0, 6 and 24 hr post-faecal incoulum.

Fermentation Endpoint Measurements (Day 2 and 3)

(i) SCFA Measurements (0, 6, 24 hr)

A 4 ml aliquot of fermentation broth was added to a 15 ml plastic cortex tube containing 1.25 mls of 20% (w/v) metaphosphoric acid. Tubes were inverted and kept at room temperature for 30 mins to enable acids to precipitate prior to storage at −80° C. before analysis by gas chromatography. This will detect the SCFA; acetic, propionic, N-butyric, Iso-butyric, N-valeric, Iso-valeric, caproic, Iso-caproic and heptanoic acids.

Samples were mixed thoroughly and allowed to settle. 1 ml of 0.01 M mixed standard (0.01 M of acetic propionic, iso-butyric, butyric, iso-valeric, valeric, iso-caproic and caproic acids in distilled water) or fermentation extract was pipetted into a glass test tube with a ground glass neck, and approximately 0.4 g of NaCl (HPLC grade) and 0.3 ml, 12 M $H_2SO_4$ added. 1.5 ml of tertiary butyl methyl ether (TBME, HPLC grade, 99.8% pure) was added and the mixture was shaken for 1 minute. The aqueous and solvent layers were allowed to fractionate for 15 minutes, in order that the top ether layer be partially removed (approximately 0.5 ml using a teat pipette) and placed in a 2 ml screw cap vial with a parafilm seal. These extracts were injected onto the Gas Chromatograph, and the concentration of the SCFA measured by comparison against the VFA standard solutions.

(ii) Gas Measurements (6, 24 hr)

The 6 and 24 hr time point bottles were removed from the anaerobic cabinet. The "tear-off" metal seal was lifted up to allow a measurement of gas pressure within the bottle. A manometer, zeroed before each measurement, measured the change in pressure in mBar.

(iii) pH Measurements (0, 6, 24 hr)

The pH of fermentation broths was measured using a pH meter (Orion, ISE 710A) after calibration of the probe against known standards.

Results

Bacterial Fermentation End-points

The potential effects of defatted copra presscake on bacterial activity have been measured in terms of the SCFA produced, the gas generated and the pH of the in vitro fermentation broth after 6 and 24 hrs incubation in the presence of a 1% faecal inoculum. Results from 14 cat measurements have been analysed and are presented in Table 6. Results from dog (n=6) are summarised in Table 7.

Control samples that contained no external substrate produced significant levels of SCFA and gas. The basal production from the control samples has been subtracted from that in substrate-added samples to yield the production caused by the coconut endosperm fibre source. Positive values represent additional production above the basal level, and negative values show an inhibited production, or a consumption compared with controls. Negative values for pH represent a decrease of the pH (results shown in Tables 6 and 7).

(a) Total SCFA

The total level of SCFA generated increased over time (Tables 6 and 7). Defatted copra presscake led to a significant increase in total SCFA ($p<0.05$) after 6 hr above that generated in the absence of a fibre source which was observed with cat and dog. After 24 hrs a similar pattern was observed.

The total SCFA produced were investigated in more detail by characterising the constituent SCFA. In vivo acetic, propionic and butyric acids are the principle end-point of carbohydrate fermentation and account for 90% of the total SCFA in the colon. Significant ($p<0.05$) increases in acetic and propionic acids were observed after 6 and 24 hr with cat and dog (with the exception of acetic acid from cat (n=14) after 24 hr).

(i) Butyrate

Butyrate is of particular interest due to the trophic effects it can exert on colonocytes, as well as its beneficial metabolic role. The production of butyrate was significantly enhanced ($p<0.05$) above control production in the presence of defatted copra presscake after 6 and 24 hr with cat (Table 6). In the cat, after 24 hr an 80% increase in the production of butyrate from defatted copra presscake was observed. This near doubling of butyrate levels may have biological significance in vivo. An increase was observed with dog after 24 hr, but this was not significant (Table 7).

(b) Gas

Gas is a second major end product of fermentation. The major components of gas are $CO_2$, $H_2$ and $CH_4$ which result principally from carbohydrate fermentation. Gas production has been measured as an increase in pressure (mBar) over time.

After 24 hrs the defatted copra presscake fibre substrate generated a significant increase ($p<0.05$) above the levels of gas produced in the absence of fibre in cat and dog (Table 6).

TABLE 6

The production of SCFA, gas and ammonia in the absence and presence of copra cake (0.7% (w/v)) after 6 and 24 hr incubation with 1% (w/v) CAT faecal homogenates. Values are the mean of n = 14.

| CAT (n = 14) | Total SCFA# | Acetate | Propionate | Butyrate | Gas | pH |
|---|---|---|---|---|---|---|
| | | mmol/L produced | | | mBar | units |
| 6 hr | | | | | | |
| Control Production | 11.6[a] | 7.01[a] | 1.58[a] | 1.15[a] | 61.2[a] | 6.26[a] |
| SE | ±0.49 | ±0.39 | ±0.08 | ±0.04 | ±14.46 | ±0.02 |
| Copra cake | 3.28[b] | 0.75[b] | 1.74[b] | 0.73[b] | 29.3[a] | −0.54[a] |
| 24 hr | | | | | | |
| Control Production | 16.2[a] | 9.59[a] | 2.20[a] | 1.77[a] | 108.4[a] | 6.27[a] |

TABLE 6-continued

The production of SCFA, gas and ammonia in the absence and presence of copra cake (0.7% (w/v)) after 6 and 24 hr incubation with 1% (w/v) CAT faecal homogenates. Values are the mean of n = 14.

| CAT (n = 14) | Total SCFA# | Acetate mmol/L produced | Propionate | Butyrate | Gas mBar | pH units |
|---|---|---|---|---|---|---|
| SE | ±0.26 | ±0.23 | ±0.09 | ±0.05 | ±8.23 | ±0.02 |
| Copra cake | 7.27[b] | 2.59[b] | 2.26[b] | 1.47[b] | 93.0[b] | −0.47[a] |

Values with different superscripts (in any one column) differ by $p < 0.05$ within each measured endpoint.
Total SCFA is total production of acetic, propionic, N-butyric, Iso-butyric, valeric, Iso-valeric, caprioc, Iso-caproic, heptanoic acids.
SE = Standard Error

TABLE 7

The production of SCFA, gas and ammonia in the absence and presence of copra cake (0.7% (w/v) after 6 and 24 hr incubation with 1% (w/v) DOG faecal homogenates. Values are the mean of n = 6.

| DOG (n = 6) | Total SCFA# | Acetate mmol/L produced | Propionate | Butyrate | Gas mBar | pH units |
|---|---|---|---|---|---|---|
| 6 hr | | | | | | |
| Control Production | 9.81[a] | 6.09[a] | 1.27[a] | 1.16[a] | 42.4[a] | 6.28[a] |
| SE | ±0.56 | ±0.34 | ±0.11 | ±0.10 | ±12.24 | ±0.03 |
| Copra cake | 2.39[b] | 0.06[b] | 2.89[b] | −0.06[a] | 49.63[a] | −0.83[c] |
| 24 hr | | | | | | |
| Control Production | 13.9[a] | 8.74[a] | 1.88[a] | 1.63[a] | 86.3[a] | 6.27[a] |
| SE | ±0.67 | ±0.41 | ±0.18 | ±0.09 | ±10.43 | ±0.02 |
| Copra cake | 5.43[b] | 0.87[b] | 4.40[b] | 0.12[a] | 89.4[b] | −0.74[b] |

Values with different superscripts (in any one column) differ by $p < 0.05$ within each measured endpoint.
Total SCFA is total production of acetic, propionic, N-butyric, Iso-butyric, valeric, Iso-valeric, caprioc, Iso-caproic, heptanoic acids.

Conclusions

The fermentation process is driven largely by the amount and type of substrate available. This system provides an excellent method for understanding the fermentability of fibre substrates, and provides a greater understanding of the role of the microflora within the large intestine.

It has been proposed that an ideal fibre source should be a slow fermenter producing high levels of SCFA (particularly butyrate). This slow fermenting fibre would ensure that fibre with remaining fermentative capacity could reach the bacteria that inhabit the distal end of the colon. Thus it might be possible to use such a fibre source to "feed" bacteria along the entire length of the large intestine. Coconut endosperm fibre approaches the criteria for such a fibre source.

The overall fermentation of copra cake between cat and dog appears to be similar with regard to the total SCFA and gas production.

The overall results show that use of coconut endosperm fibre improves or maintains (good) faeces quality and improves or maintains (good) gastrointestinal tract health.

The significant increase in butyrate observed with cat, is an important factor that contributes to a healthy intestinal environment. In the cat, the defatted copra presscake, as a fibre source, was surprisingly good compared to other fibre sources, in that it produced a significant increase in butyrate above basal levels. Similar results were seen in the dog with defatted copra presscake although they were not as marked.

EXAMPLE 4

Introduction

The objective of the trial was to assess the faeces quality performance of two recipes containing defatted copra presscake.

The base pet foods used were canned chunks in jelly product. The recipe ingredients for each diet was:

| Diet (Chunks Recipe) | Recipe 1 | Recipe 2 |
|---|---|---|
| Gravy | 50 | 42 |
| Meat and protein source | 43 | 45.5 |
| Wheat Starch | 1 | 1 |
| Salts | 0.5 | 0.4 |
| Additional Water | 5 | 10 |
| Deffated Copra Presscake | 1.9 | 1.1 |
| Total (%) | 105.9 | 100.00 |

Recipe 1 total is higher than 100% due to oven loss (oven yield 90%). All cans were processed at 125° C. for 61 minutes.

Method

The faeces quality was measured in a two-week cross-over trial, on a panel of 10 adult dogs representing a number of different breeds.

The dogs used for the trial were:

Beagle 1
Beagle 2
Beagle 3
Beagle 4
Beagle 5
English Springer Spaniel 6
English Springer Spaniel 7
Golden Retriever 8
Cairn Terrier 9
Miniature Schnauzer 10

The dogs were offered the following amounts of diet each day (g/day based on maintenance feeding levels):

| Beagle 1 | Beagle 2 | Beagle 3 | Beagle 4 | Beagle 5 | English Springer Spaniel 6 | English Springer Spaniel 7 | Golden Retriever 8 | Cairn Terrier 9 | Miniature Schnauzer 10 |
|---|---|---|---|---|---|---|---|---|---|
| 1200 | 1400 | 1200 | 1100 | 1100 | 1100 | 1500 | 2000 | 600 | 500 |

Before the start of each trial week the dogs were fed a standard pet food with the following recipe for 2 days. This routine practice ensures a common base line for the faeces screening studies.

| Diet Recipe | |
|---|---|
| Fish and poultry | 35% |
| Cereals (maize, wheat) | 20% |
| Gravy | 45% |

Faeces quality was measured subjectively using the 17 category faeces scoring scale, whereby all defecations were graded (in quarter grades) between 1 and 5 (see Appendix 1). The mean faeces score was calculated for each dog using all faeces scores collected during the trial period. An overall mean faeces score for the diet was calculated by averaging the means for each dog. Statistical analysis was conducted using 2-way ANOVA (with diet as a fixed factor and dog as a variable factor).

Results

Acceptance

All dogs ate 100% of the food offered over the two-week trial.

Faeces Quality

Overall faeces quality was excellent for both diets, when classified according to the mean faeces score.

There was no significant difference in mean faeces score between the two diets at either the 95% or 90% confidence level (ANOVA, p=−0.77).

| | | Recipe 1 | Recipe 2 |
|---|---|---|---|
| Faeces Quality | Mean Score | 2.3 | 2.3 |
| | No. Defecations | 200 | 207 |

FIG. 1 shows a comparison of mean faeces score and 95% LSD (Least Square Difference) intervals for the diets.

| Nutrient content of the diet (% As Is) | | |
|---|---|---|
| | Recipe 1 | Recipe 2 |
| Moisture | 81.9 | 82 |
| Protein | 7.5 | 6.9 |
| Fat | 5.4 | 6.4 |
| Ash | 2.9 | 2.2 |
| Crude Fibre (AOAC) | 0.2 | 0.3 |
| Insoluble Fibre (AOAC) | 1.9 | 1.5 |
| Soluble Fibre (AOAC) | 0.9 | 0.8 |

Discussion

Overall faeces quality was excellent for both diets, when classified according to the mean score faeces.

There was no significant difference in mean faeces score between the two diets at either the 95% or 90% confidence level (ANOVA, p=0.77).

EXAMPLE 5

Introduction

The objective of the trial was to assess the faeces quality performances of a dry recipe containing copra presscake.

The base pet food used was an extruded mono component dry product. The recipe ingredients are as follows:

| Diet | Recipe |
|---|---|
| Poultry | 13 |
| Cereals (Wheat & Maize) | 17 |
| Minerals | 5 |
| Fat | 5 |
| Copra Presscake | 5 |
| Total (%) | 100 |

Method

The faeces quality was measured in a one week trial, on a panel of 14 adult dogs representing a number of different breeds.

The dogs used for trial were:

1 Labrador Retriever
3 Border Collies
2 German Shepherd Dogs
1 Yorkshire Terrier
2 Sussex Spaniels
5 Cross Breeds The dogs were fed to maintenance energy requirements.

Faeces quality was measured subjectively using the 9 category faeces scoring scale, whereby all defections were graded (in half grades) between 1 and 5 (see Appendix 1). The mean faeces score was calculated for each dog using all faeces scores collected during the trial period. An overall mean faeces score for the diet was calculated by averaging the means for each dog.

Results

Acceptance

All dogs ate 100% of the food offered over the one week trial.

Faeces Quality

Overall faeces quality was excellent for the product, when classified according to the mean faeces score.

Mean faeces score was 2.5.

Conclusion

The use of defatted copra in a dry product gives ideal faeces quality.

EXAMPLE 6

Investigation into the effect of coconut endosperm fibre on the survival of Campylobacter in the canine intestine.

Summary

Campylobacter is one of the most predominant gastrointestinal pathogens causing both clinical and non-clinical infections in dogs.

An in vitro model of the canine large intestine has been developed to test the effect of novel fibres on the survival of canine bacterial pathogens.

Inclusion of coconut endosperm fibre in this model resulted in the elimination of viable *Campyobacter jejuni* cells from the system.

Methods

1. *C. jejuni* cells were grown from stock cultures and cultured at 37° C. under microaerobic conditions (5% $O_2$, 10% $CO_2$ and 85% $N_2$). Liquid cultures were grown in 20 ml volumes in 50 ml conical flasks shaken on an orbital shaker. Overnight cultures grown in Mueller Hinton (MH) broth (Oxoid) were adjusted to $A_{600}$ 1.0 before incusion in the assay.
2. Flasks were set up with 200 ml MH broth, 1 ml of the adjusted *C. jejuni* culture, and 2 g fresh faeces. To test flasks, 0.7% (w/v) copra cake was added and swirled to mix. Control flasks had no further additions.
3. Flasks were sampled at the start (0 hours) and end (24 hours) of the experiment to determine viable counts of *C. jejuni* cells by serially diluting samples from the flasks and plating dilutions on to Campylobacter selective agar (LabM). Plates were incubated microaerobically for 48 hours, after which viable numbers were determined.
4. At the end of the experiment the pH of the mixture in each flask was etermined using Multistix (Bayer).
5. The experiment was conducted six times using a faecal sample from a different dog each time. All dogs were fed a commercially available premium (complete and balanced) dry food for the duration of the study.

Results

After a 24 hour microaerobic incubation, no viable *C. jejuni* cells could be recovered from flasks that had coconut endosperm fibre added. In contrast, *C. jejuni* cells were recovered from the flasks that contained no coconut endosperm fibre at around $10^8$ cells per ml. The results from the 6 individual experiments are shown in the table below and the graph that follows summarises the data: Numbers of viable *Campylobacter jejuni* cells ($\log^{10}$) recovered from the model of the canine large intestine with and without the addition of coconut endosperm fibre.

| Faecal Sample (Dog No) | 0 hours < +0.7% | 0 hours Coconut None | 24 hours Endosperm +0.7% | 24 hours Fibre > None |
|---|---|---|---|---|
| <----------$\log^{10}$ colony forming units of *C. jejuni*----------> | | | | |
| 1 | 7.76 | 7.75 | 0 | 7.25 |
| 2 | 7.33 | 7.64 | 0 | 8.56 |
| 3 | 7.77 | 7.75 | 0 | 7.17 |
| 4 | 7.72 | 7.74 | 0 | 7.47 |
| 5 | 7.67 | 7.71 | 0 | 8.59 |
| 6 | 7.16 | 7.38 | 0 | 8.97 |
| Mean | 7.57 | 7.66 | 0 | 8 |
| STD | 0.26 | 0.14 | 0 | 0.79 |

FIG. 2 shows a graph of the effect of the inclusion of coconut endosperm fibre in the canine large intestine model on the survival of *Campylobacter jejuni*. Letters denote statistically significant difference.

Recorded pH after 24 hours incubation with coconut endosperm fibre included and omitted from the system for each dog.

| Dog No. | +0.7% Coconut endosperm fibre | No Coconut endosperm fibre |
|---|---|---|
| 1 | 6.75 | 7.5 |
| 2 | 6.25 | 7.5 |
| 3 | 6.75 | 7.5 |
| 4 | 6.25 | 7.5 |
| 5 | 6.25 | 7.5 |
| 6 | 6.25 | 7.5 |

At the end of the incubation period the pH of the solutions in each flask was measured and was found to be 7.5 when coconut endosperm fibre was omitted from the system (SD of 0). When coconut endosperm fibre was included in the model, the pH was found to be 6.42 (SD of 0.26).

Conclusions

Inclusion of coconut endosperm fibre in a model of the canine large intestine resulted in the elimination of viable *Campylobacter jejuni* cells. With no coconut endosperm fibre added to the system, *C. jejuni* cells showed no loss in viability for the duration of the experiment. As a pH range of 6.5 to 7.5 is optimum for Campylobacter, it is unlikely that the difference in pH observed between the two conditions was responsible for the difference observed in survival. Instead, it is likely that the non-pathogenic, saccharolytic bacteria present in the faeces metabolise the coconut endosperm fibre. *C. jejuni* is incapable of fermenting carbohydrates, thus the coconut endosperm fibre being present gives the non-pathogenic, saccharolytic bacteria an advantage.

EXAMPLE 7

In this study, the inflammatory status of the colon after a feeding diet containing coconut endosperm fibre sources and a standard (no fibre) diet were compared

Methods

The trial involved 7 dogs representing a number of breeds. Dogs were housed individually for the duration of the feeding and measurement periods. The trial was carried out as a cross-over. Dogs were fed the diet solus in amounts required to maintain body weight ($125 \times BW^{0.75}$) with access to drinking water at all times for 4 weeks with a one week washout. The test diet was a nutritionally complete wet format that consisted of oven formed meat chunks that were canned in water. Coconut endosperm fibre was included at 7.2% (w/w). All other recipe components were reduced pro rata for the inclusion of coconut endosperm fibre in the form of copra cake. The washout diet was a complete and balanced diet.

Culture of Biopsy Samples

Three biopsies were taken from mid-colon, transported in tissue culture media (RPMI plus gentomycin) and weighed. The biopsy samples were washed in fresh media for 30 minutes and transferred to a fresh 24-well multiwell plate containing 1 ml of media and cultured for 24 hours at 37° C. with 5% $CO_2$. The biopsy samples were then spun down at 13000 rpm for 5 minutes and the supernatant transferred to a fresh eppendorf tube and frozen at −20° C. until required. 0.5 ml of 1% triton lysis buffer (20 mM Tris Ph7.5, 20 mM $NaCl_2$, 1% triton×100) was added to the biopsy sample and left for a minimum of 1 hour. The samples were then homogenised briefly and total protein content measured using Sigma Microprotein-PR™ kit. Total biopsy protein was found to significantly correlate with biopsy wet weight and used to standardise eicosanoid production to biopsy sample size.

Measurement of Eicosanoid Production

Levels of $PGE_2$ production by mid-colonic biopsy samples were measured by enzyme immunoassay (EIA). Supernatant samples were diluted 1 in 10 in fresh media. $PGE_2$ EIA tests were obtained from R&D Systems and performed as described in provided protocol sheets. In short, 100 ul sample and $PGE_2$ standard was added to 96 well microplate previously coated with goat anti-mouse/rabbit polyclonal antibody. 50 µl $PGE_2$ conjugated to alkaline phosphatase and 50 µl mouse polyclonal antibody to $PGE_2$ were added. The plate was incubated for 2 hours at room temperature on a horizontal orbital plate shaker set at 500±50 rpm. After incubation the plate was washed and 200 µl pNPP substrate added. After an hour incubation, 50 µl stop solution (trisodium phosphate) was added and the optical density of each well determined immediately using a microplate reader set to 450 nm wavelength. Concentration of eicosanoids per mg biopsy protein was calculated from a standard curve.

Results

Eicosanoid production by colonic biopsy samples.

When dogs were fed the coconut endosperm fibre containing diet biopsies produced significantly less $PGE_2$ than when dogs were fed the standard diet (P=0.08). The results are summarised below in the table below and FIG. 3 which shows mean $PGE_2$ production by colonic biopsy samples.

| $PGE_2$ production by biopsy samples | |
|---|---|
| Diet (Fibre Source) | $PGE_2$ production (ng/mg protein) |
| Standard (No fibre) | 242.3 ± 182.1(a) |
| Coconut endosperm fibre | 105.4 ± 55.5(b) |

Same letter denotes no significant difference (p < 0.1)

Appendix 1—Faeces Quality

The 17 point scoring scale is used to assess all defecations, whereby faeces are scored in quarter grade increments between grade 1 and grade 5.

If a faeces is judged not be a full or the adjacent half grade it is scored as a quarter grade. The half grade demarcations are below.

The 9 point scoring scale is used to assess all defecations, whereby faeces are scored in half grade increments between grade 1 and grade 5. The half grade demarcations are:

Grade 5—Watery diarrhoea

Grade 4.5—Diarrhoea with some areas of consistency

Grade 4—The majority, if not all of the form is lost, poor consistency, viscous

Grade 3.5—Very moist, but still has some definite form

Grade 3—Moist, beginning to lose form, leaving a definite mark when picked up

Grade 2.5—Well formed, slightly moist surface, leaves a mark, sticky to touch

Grade 2—Well formed, does not leave a mark, 'kickable'

Grade 1.5—Hard and dry

Grade 1—Hard, dry and crumbly, 'bullet-like'

Below is an example of the scoring scale with an indication of the 'ideal' and 'unacceptable' ranges for faeces quality:

Unacceptable (or poor faeces quality) (U)=Less than 1.5 and greater than 3.5 (exclusive)

Ideal (I)=Between 1.5 and 2.5 (inclusive)

The mean faeces score produced by each dog is calculated and then an overall mean is determined for the whole trial by averaging the mean faeces scores from each dog.

Appendix 2

The Englyst method, from Englyst and Cummings (Supra).

Experimental

Apparatus

The fractionation procedure was carried out in 50–60 ml screw-topped glass centrifuge tubes as previously described. Gas-liquid chromatography was performed with a Pye Unicam Series 204 chromatograph, fitted with a flame-ionisation detector. A 2.1 m×2 mm i.d. glass column packed with Supelcoport (100–200 mesh) coated with 3% SP 2330 was used. The column temperature was 215° C. (isothermal) and the injector and detector temperatures were 250° C. The carrier gas (nitrogen) flow-rate was 20 ml min–$^1$.

Reagents

High purity certified reagents were used for all analyses. Enzyme preparations were as follows: hog pancreatic α-amylase, E.C.3.2.1.1. (Sigma, Cat. No. A4268); pullulanase, E.C.3.2.1.41. (Boehringer, Cat. No. 108944).

Method

The sequence of steps iin the procedure is summarised in FIG. 1.

Pre-treatment of Sample

As far as possible, foods should be analysed without any pre-treatment. If there are problems in taking a representative sample, foods with a low water content can be ball milled for 2–3 minutes, and those with a higher water content homogenised, or freeze-dried and ball milled.

Sample Mass

Accurately weigh between 50 and 1,000 mg of sample, containing not more than 150 mg of starch and 50 mg of NSP, into a 50–60 ml screw-top centrifuge tube and add a stirrer.

Fat Extraction and Drying

Samples with dry matter between 90 and 100% and with less than 203% of fat can be analysed directly. Otherwise, add 40 ml of acetone, mix for 30 minutes by using a magnetic stirrer, centrifuge and remove by aspiration as much of the supernatant as possible without disturbing the residue. Place the tubes in a water bath at 65° C. on a magnetic stirrer hot plate and mix the residue for a few minutes until it appears to be dry. The beaker can be covered and the acetone vapour removed by water pump.

Dispersion of the Starch

Add 2 ml of DMSO, cap the tube and heat it in a boiling water bath for 1 hour, timed from when re-boiling commences, stirring continuously. Then, without cooling, add 8 ml of 0.1 M sodium acetate buffer pH5.2, at 50° C. and vortex mix immediately.

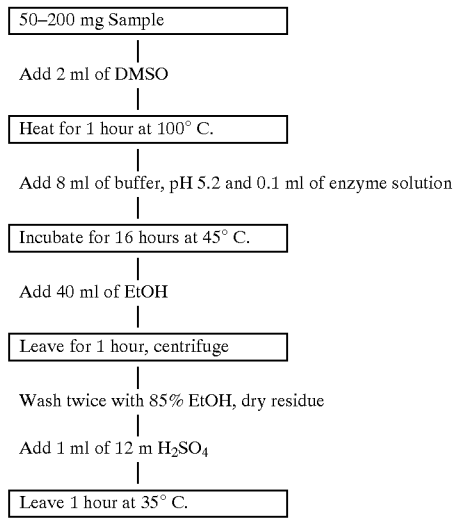

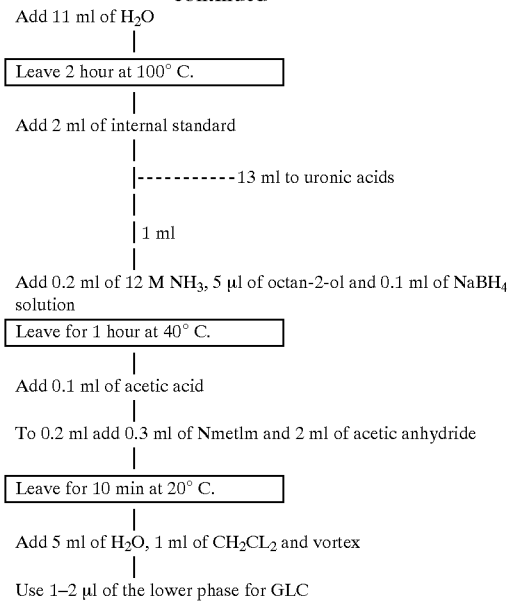

Procedure for the analysis of non-starch polysaccharides (NSP)

Enzyme Hydrolysis of the Starch

Cool the tube to 45° C. and immediately add 0.1 ml of an enzyme solution containing 5,000 units of α-amylase and 5 units of pullulanase per ml of acetate buffer at pH 5.2. Incubate the samples at 450C for 16–18 hours, preferably mixing continuously as described previously.

Following the enzyme treatment, add 40 ml of absolute ethanol, mix well and leave to stand for 1 hour at room temperature. Centrifuge for 10 minutes or until-a clear supernatant liquid is obtained. Removed by aspiration as much of the supernatant liquid as possible, without disturbing the residue, and discard it. Wash the residue twice with 50 ml of 85% ethanol by mixing to form a suspension, centrifuging until clear and removing the supernatant liquid as before. Add 40 ml of acetone to the washed residue, stir for 5 minutes and then centrifuge. Remove the supernatant liquid by aspiration and dry the residue as described under Fat extraction and drying.

Acid Hydrolysis of the Residue From Enzymic Digestion

Disperse the dried residue in 1 ml of 12 M sulphuric acid, using a vortex mixer. Leave at 35° C. for 1 hour to solubilise the cellulose, then rapidly add 11 ml of water and mix.

Heat the solution in a boiling water bath for 2 hours from re-boiling, stirring continuously. Cool it to room temperature by placing the tube in water, add 2 ml of internal standard (2 mg of allose per ml of saturated benzoic acid solution) and mix the contents of the tube. Use 1 ml of the hydrolysate for the preparation of alditol acetates and keep the remainder for the determination of uronic acids.

Uronic Acids

The method used is a modification of the method of Scott. Mix 0.3 ml of hydrolysate (diluted, if necessary, so that it contains between 25 and 100 $\mu$g of uronic acids per ml) with 0.3 ml of a mixtures of sodium chloride-boric acid solution (prepared by adding 2 g of sodium chloride and 3 g of boric acid to 100 ml of water) Add 5 ml of concentrated sulphuric acid and vortex mix, then place the tube in a heating block at 70° C. Leave the tube and contents for 40 minutes and then cool them to room temperature by placing in water. When cool, add 0.2 ml of 3.5-dimethylphenol solution (0.1 g of $(CH_3)_2$—$C_6H_3OH$ in 100 ml of glacial acetic acid) and mix immediately. Between 10 and 15 minutes later read the absorbance at 400 and 450 nm in a spectrophotometer against a water reference. Subtract the reading at 400 nm from that at 450 nm for each sample and plot the difference obtained for glucuronic acid standards (over the range 25–125 $\mu f$ ml$^{-1}$). Read the sample concentrations from the graph.

Preparation of Alditol Acetates

To 1 ml of hydrolysate add 0.2 ml of 12 M ammonia solution and 5 $\mu l$ of octan-2-ol. Test that the solution is alkaline, and then add 0.1 ml of a freshly prepared solution of 100 mg of sodium tetrahydroborate (III) (sodium borohydride) per ml of 3 M ammonia solution. Mix, leave the mixture for 1 hour at 40° C. and add 0.1 ml of glacial acetic acid. Next, to 0.2 ml of the acidified solution add 0.3 ml of N-methylimidazole and 2 ml of acetic anhydride, and mix. Leave it for 10 minutes at 20° C. (room temperature), add 5 ml of water, mix, and when cooled add 1 ml of dichloromethane, agitate the contents vigorously on a vortex mixer and centrifuge for a few minutes to separate the mixture into two phases. Remove the bulk of the upper phase by aspiration and discard it, then transfer the lower phase to a small vial, seal and store it at −20° C. Use 1–2 $\mu l$ for injection on to the chromatograph.

Alternative Preparative of Alditol Acetates

When dichloromethane is used as a solvent for the alditol acetates it has been observed in a number of laboratories without automatic GLC injection facilities that the injection technique is critical to the obtaining of reproducible results. A more robust method can be obtained if dichloromethane is replaced with ethyl acetate as a solvent for alditol acetates. The procedure is as follows:

To 1 ml of hydrolysate add 0.2 ml of 12 M ammonia solution and 5 $\mu l$ of octan-2-ol. Test that the solution is alkaline, then add 0.1 ml of a freshly prepared solution of 100 mg of sodium tetrahydroborate (III) per ml of 3 M ammonia solution. Mix, leave the mixture for 1 hour at 40° C. and add 0.1 ml of glacial acetic acid. To 0.5 ml of the acidified solution add 0.5 ml of N-methylimidazole, 5 ml of acetic anhydride and mix.

Leave for 10 minutes at 20° C. (room temperature), then add 0.6 ml of ethanol and mix. After 5 minutes add 5 ml of water, place in a water bath at room temperature, add 5 ml of 7.5 M KOH and a few minutes later a further 5 ml of 7.5 M KOH. Mix by inverting and leave to separate into two phases. Transfer the top phase to a small vial and store at +5° C. Use 1–2 $\mu l$ for injection on the chromatograph.

Other Embodiments

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. A pet food product comprising a coconut endosperm fibre as a dietary fibre component in the pet food product wherein the pet food product does not include an elastic hydrous gel comprising a synergistic mixture of coconut endosperm and carrageena or hemicellulose.

2. The pet food product of claim 1, wherein the coconut endosperm fibre is in the form of copra, defatted copra, fresh coconut endosperm, coconut flour or desiccated coconut.

3. The pet food product of claim 1, wherein the dietary fibre, is present at a level of from 0.15 to 5%, on a dry matter basis, in the pet food product.

4. The pet food product of claim 2, wherein defatted copra is present at a level of from 0.5 to 15% on a dry matter basis of the pet food product.

5. A process for preparing a pet food product as claimed in claim 1, comprising the steps of mixing the ingredients, with an optional step of heating/cooking.

6. A method of using a pet food product comprising the step of feeding an animal a pet food product as claimed in claim 1.

7. A process of using coconut endosperm fibre, the process comprising the use of coconut endosperm fibre as a dietary fibre component in a pet food product.

8. The process of claim 7, wherein the coconut endosperm fibre is in the form of copra, defatted copra, fresh coconut endosperm, coconut flour or desiccated coconut.

9. The process of claim 7, wherein the dietary fibre, is present at a level of from 0.15 to 5%, on a dry matter basis, of the pet food product.

10. The process of claim 8, wherein the defatted copra is present at a level of from 0.5 to 15% on a dry matter basis, in the pet food product.

11. A process of using coconut endosperm fibre in the manufacture of a pet food product, the process comprising the use of coconut endosperm fibre as a dietary fibre component in the pet food product wherein the pet food product does not include an elastic hydrous gel comprising a synergistic mixture of coconut endosperm and carrageenan or hemicellulose.

12. A process of using coconut endosperm fibre in the manufacture of a pet food product, the process comprising the use of coconut endosperm fibre as a dietary fibre component in the pet food product for the prevention or treatment of poor faeces quality.

13. A process of using coconut endosperm fibre in the manufacture of a pet food product, the process comprising the use of coconut endosperm fibre as a dietary fibre component in the pet food product for maintaining or improving gastrointestinal tract health.

14. The process of claims 11, 12 or 13, wherein the coconut endosperm fibre is in the form of copra, defatted copra, fresh coconut endosperm, coconut flour or desiccated coconut.

15. The process of claims 11, 12 or 13, wherein the dietary fibre, is present at a level of from 0.15 to 5%, on a dry matter basis, of the pet food product.

16. The process of claim 14, wherein the defatted copra is present at a level of from 0.5 to 15% on a dry matter basis, in the pet food product.

17. A process of using coconut endosperm fibre in the manufacture of a pet food product, the process comprising the use of coconut endosperm fibre for the prevention or treatment of pathogenic bacteria in the large intestine of a pet animal.

18. The process of claim 17, wherein the coconut endosperm fibre is in the form of copra, defatted copra, fresh coconut endosperm, coconut flour or desiccated coconut.

19. The process of claim 17, wherein the pathogenic bacteria is Campylobacter, Salmonella or *Escherchia coli*.

20. The process of claim 17, wherein the pet animal is a canine animal.

21. A method for the prevention or treatments of a pathogenic bacterial infection in the large intestine of a pet animal, the method comprising feeding said pet animal a pet food product containing coconut endosperm fibre.

22. The method of claim 21, wherein the coconut endosperm fibre is in the form of copra, defatted copra, fresh coconut endosperm, coconut flour or desiccated copra, fresh coconut endosperm, coconut flour or desiccated coconut.

23. The method of claim 21, wherein the pathogenic bacteria is Campylobacter, Salmonella, or *Escherchia coli*.

24. The method of claim 21, wherein the pet animal is a canine animal.

25. A process of using coconut endosperm fibre in the manufacture of a pet food product, the process comprises the use of coconut endosperm for the prevention or treatment of intestinal inflammation of a pet animal.

26. The process of claim 25, wherein the coconut endosperm fibre is in the form of copra, defatted copra, fresh coconut endosperm, coconut flour or desiccated coconut.

27. The process of claim 25, wherein the pet animal is a canine animal.

28. A method for the prevention or treatment of intestinal inflammation in an animal, the method comprising feeding said animal a pet food product comprising coconut endosperm fibre.

29. The method of claim 28, wherein the coconut endosperm fibre is in the form of copra, defatted copra, fresh coconut endosperm, coconut flour or desiccated copra, fresh coconut endosperm, coconut flour or desiccated coconut.

30. The method of claim 28, wherein the animal is a canine animal.

* * * * *

UNITED STATES PATENT AND TRADEMARK OFFICE
CERTIFICATE OF CORRECTION

PATENT NO. : 6,656,512 B1
DATED : December 2, 2003
INVENTOR(S) : Janel Fone et al.

It is certified that error appears in the above-identified patent and that said Letters Patent is hereby corrected as shown below:

<u>Column 26,</u>
Line 5, delete "carrageena" and insert -- carrageenan. --

Signed and Sealed this

Fourteenth Day of September, 2004

JON W. DUDAS
*Director of the United States Patent and Trademark Office*